Jan. 19, 1937 E. C. JOHNSON Plant Pat. 221
LOBELIA
Filed July 22, 1936
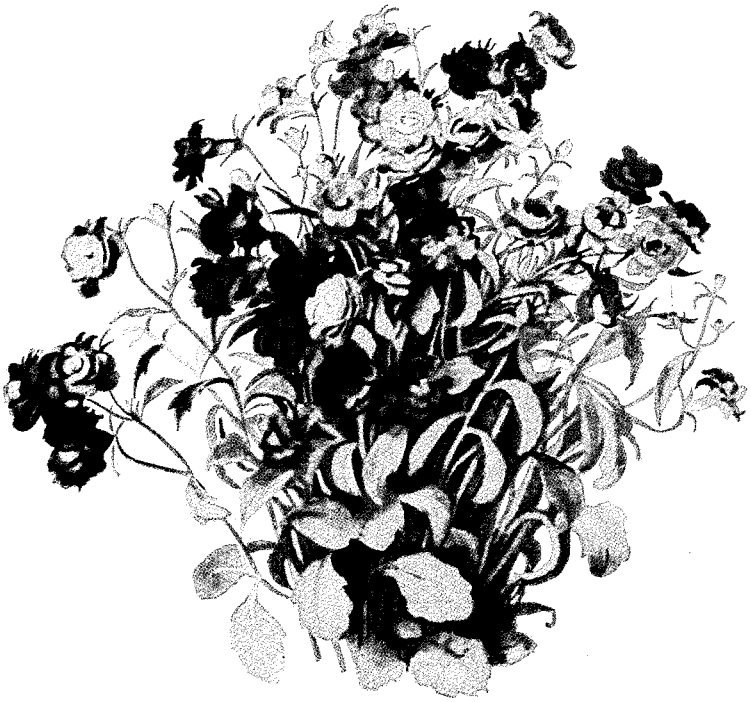
INVENTOR
Esther C. Johnson
BY A. B. Bowman
ATTORNEY Patented Jan. 19, 1937

Plant Pat. 221

UNITED STATES PATENT OFFICE

221

LOBELIA

Esther C. Johnson, La Mesa, Calif.

Application July 22, 1936, Serial No. 91,880

1 Claim. (Cl. 47—60)

My invention or discovery relates to a new variety of Lobelia and may be described as a sport of Lobelia, particularly of the trailing Lobelia known as *Lobelia erinus gracilis*, and as such it is unique and novel because, so far as I am aware, no Lobelia of this character exists which produces a double flat rosette flower in form.

The accompanying illustration shows in full color a complete flowering plant with some buds and some fully opened flowers as well as foliage and stems.

This new Lobelia is a very profuse bloomer and shows some bloom through the winter months and blossoms profusely over a period of six months beginning in April and is a perennial and does not produce seed.

This new Lobelia has been asexually propagated and found to produce true to form. The following is a more detailed description of this new Lobelia:

*Parentage*

Sport of *Lobelia erinus gracilis*.

*Classification*

Small compact bush plant four to five inches in height.

*Flower*

Blossoms profusely over a period of six months beginning in April; is very double flat and rosette in form, three-eighths to one-half inch in diameter; color ultramarine blue; has five linear sepals acutely pointed; the flower has an extended tapered stem portion, the end of which unites with the stem of the plant; its color varies somewhat from light blue to ultramarine blue as the flower ages; the buds just before opening have a light red tint.

*Plant*

The leaves are linear, lanceolate at the top, widened down towards the stem to spatulate with several distinct notches; the juvenile leaf orbiculate to ovate; the stem and branches are triangular in cross section; the plant grows from four to five inches tall.

It distinguishes from the variety *Lobelia erinus gracilis* from which it is a sport in that it is a small compact plant and not a trailing Lobelia in form, and its very double flat rosette flower of ultramarine blue is also a distinguishing characteristic.

Having thus described my invention, I claim:

A new and distinct variety of Lobelia, herein shown and described, characterized particularly by its very double, flat rosette form of flower of ultramarine blue with five linear sepals acutely pointed and the plant compact and perennial.

ESTHER C. JOHNSON.